Figure 1:
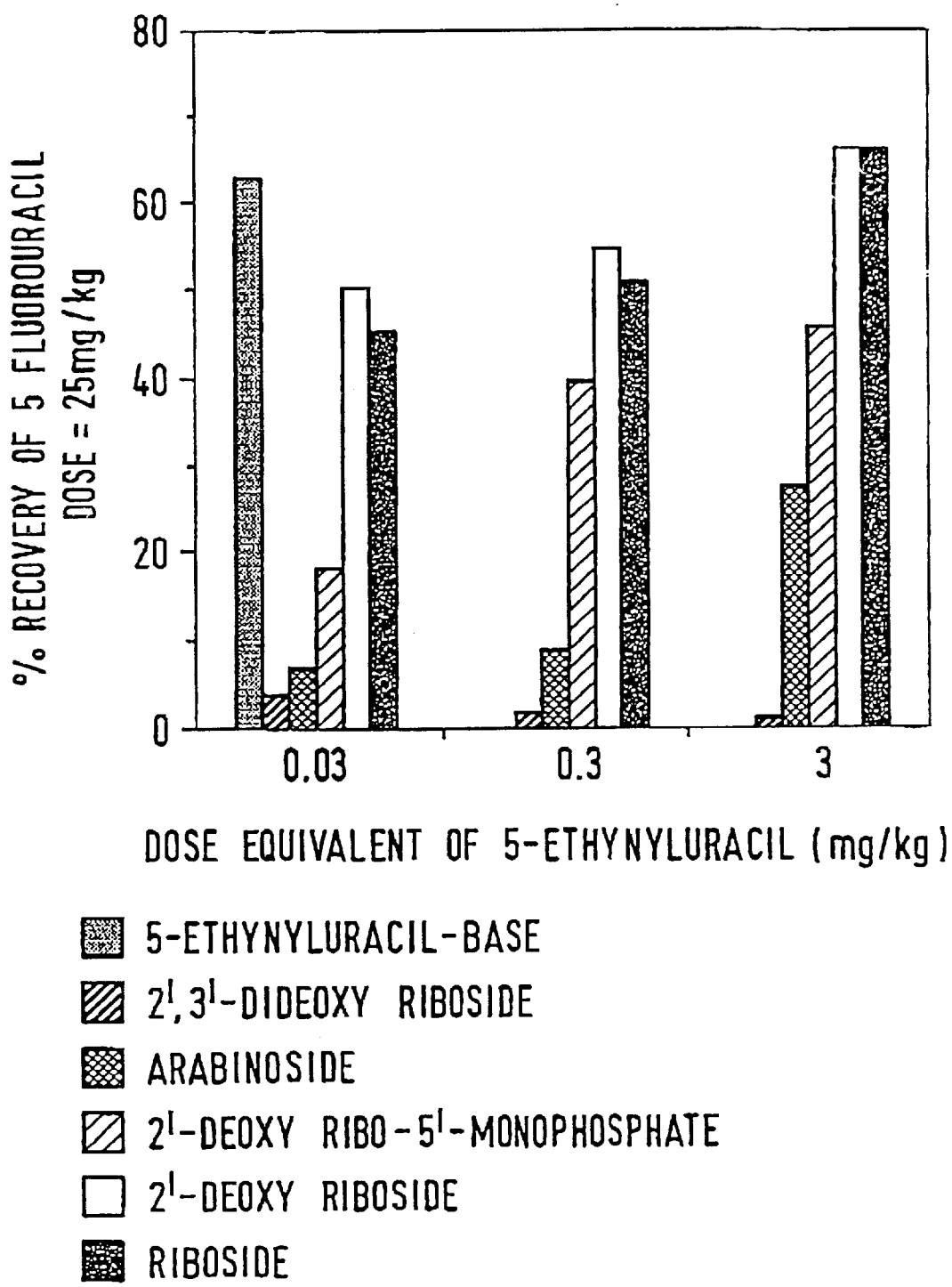

United States Patent

Boyd et al.

Patent Number: 5,843,917
Date of Patent: Dec. 1, 1998

[54] 5-FLUOROURACIL DERIVATIVES

[75] Inventors: Frank Leslie Boyd, Raleigh; Thomas Anthony Krenitsky, Chapel Hill, both of N.C.

[73] Assignee: Glaxo Wellcome Inc., Five Moore Drive, N.C.

[21] Appl. No.: 612,911

[22] PCT Filed: Nov. 4, 1994

[86] PCT No.: PCT/GB94/02428

§ 371 Date: May 2, 1996

§ 102(e) Date: May 2, 1996

[87] PCT Pub. No.: WO95/12606

PCT Pub. Date: May 11, 1995

[30] Foreign Application Priority Data

Nov. 5, 1993 [GB] United Kingdom ............ 9322795

[51] Int. Cl.⁶ .................. A61K 31/70; C07H 19/10; C07D 239/02

[52] U.S. Cl. .................. 514/50; 514/256; 536/28.5; 536/28.55; 536/28.52; 536/28.54; 544/316; 544/336

[58] Field of Search .................. 544/316, 336; 514/256, 50; 536/28.5, 28.55, 28.52, 28.54

[56] References Cited

U.S. PATENT DOCUMENTS 5,457,187 10/1995 Gmeiner et al. .................. 536/25.5

FOREIGN PATENT DOCUMENTS

| 436902   | 7/1991 | European Pat. Off. |
| 1620631  | 2/1970 | Germany. |
| 2066812  | 7/1981 | United Kingdom. |
| 92/01452 | 2/1992 | WIPO. |
| 92/04901 | 4/1994 | WIPO. |

OTHER PUBLICATIONS

Koronaik et al., Biochemical and Biophysical Research communications, (1987), vol. 146, No. 3.

Fischel et al. Clin. Cancer Res., (1995), 1 (9), 991–6.

Spector Thomas, Curr. Opin. Ther. Pat. (1993), 3(12) 1751–4.

Martinez et al., (J. Org. Chem. 31 (10), pp. 3263–3267, 1996).

Mukherjee et al., (Cancer Rsearch, vol. 22, (1962), pp. 815–822).

Kroeger et al. (Biochemistry, vol. 2, (1963), pp. 566–572.

Gasparini et al. (CA:122:213, abstract of Biochem. Pharmacol. (1994), 48(6), 1121–8.

Primary Examiner—José G. Dees
Assistant Examiner—Sabiha N. Qazi
Attorney, Agent, or Firm—Robert T. Hrubiec

[57] ABSTRACT

Novel compounds comprising 5-fluorouracil or 5-fluorouridine covalently linked to 5-ethynyluracil, 5-ethynyluridine or 5-propynyluracil and pharmaceutical compositions comprising such compounds are disclosed.

3 Claims, 1 Drawing Sheet

5-FLUOROURACIL DERIVATIVES

This application is filed pursuant to 35 U.S.C. § 371 as a United States National Phase Application of International Application No. PCT/GB94/02428 filed Nov. 4, 1994 which claims priority from GB9322795.7 filed Nov. 5, 1993.

The present invention relates to compounds which comprise certain enzyme inactivators which are useful in medicine, particularly cancer chemotherapy, covalently linked to antineoplastic agents, particulary 5-fluorouracil (5-FU).

5-Fluorouracil has been used in cancer chemotherapy since 1957. Sensitive tumours include breast cancer, gastrointestinal malignancies, and cancers of the head and neck; 5-fluorouracil is also used as a radiation sensitiser. 5-Fluorouracil is metabolised rapidly in the liver (half-life between 8 and 20 minutes) by the enzyme dihydrothymidine dehydrogenase (uracil reductase). It has been reported (Cancer Research 46, 1094, 1986) that 5-(2-bromovinyl)-uracil (BVU) is an inhibitor of dihydrothymidine dehydrogenase which both retards the metabolism of 5-fluorouracil and enhances its antitumour activity. It has been reported that 5-(2-bromovinyl)-2'-deoxyuridine (which is metabolised in vivo to BVU) enhances the antitumour activity of 5-fluorouracil and 5-deoxy-5-fluorouridine, a prodrug of 5-fluorouracil (Biochemical Pharmacology 38; 2885, 1989).

WO92/04901 discloses 5-substituted uracil derivatives which are useful as inactivators of uracil reductase; they increase the level and half-life of 5-fluorouracil in plasma and enhance the activity of 5-fluorouracil. These derivatives also reduce the normally encountered variations of 5-fluorouracil plasma levels between subjects. 5-ethynyluracil is 100-fold more potent than BVU as an inactivator of uracil reductase.

It has now been found that useful compounds can be produced by covalently linking a uracil reductase inactivator moiety with a 5-fluorouracil moiety or a prodrug thereof.

Therefore a first aspect the present invention provides a compound of the formula:

$$X-L-Y \qquad (I)$$

wherein X represents a uracil reductase inactivator or prodrug thereof, Y represents 5-fluorouracil or a prodrug thereof, and L is a linking group covalently linked to both X and Y. Preferably X is a 5-substituted or 5,6-dihydro-5-substituted uracil derivative, the 5-substituent being bromo, iodo, cyano, halo-substituted $C_{1-4}$ alkyl, $C_{2-6}$ alkenyl, halo substituted $C_{2-6}$ alkenyl group, a $C_{2-6}$ alkynyl group, halo substituted $C_{2-6}$ alkynyl group.

These compounds when administered to a subject, for example a mammal such as a human, provide both a uracil reductase inactivator as well as the 5-fluorouracil antineoplastic agent itself. Thus, only a single active agent need be administered to a subject.

In addition, these compounds have the advantage that they can be administered orally. 5-Fluorouracil cannot normally be administered orally, as it is destroyed by uracil reductase in the gastrointestinal tract. A single agent, which provides 5-FU and which can be administered orally, is now provided.

By a $C_{2-6}$ alkenyl or $C_{2-6}$ alkynyl group is meant a straight or branched chain alkenyl or alkynyl group, the latter including an alkenyl or alkynyl group substituted by a $C_{2-6}$ cycloalkyl group.

The halogen substituent on the alkenyl or alkynyl group is preferably bromo, chloro or iodo. Halo-substituted ethenyl and ethynyl groups are particularly preferred. Usually only one halo substituent will be present. Preferred halo-substituted alkenyl groups are substituted in the 1-position.

The uracil derivative moiety is preferably one wherein the 5-substituent is a $C_{2-6}$ alkynyl group (optionally halo-substituted), conveniently a $C_{2-4}$ alkynyl group and preferably an ethynyl or propynyl group. In preferred 1-haloalkenyl and alkynyl derivatives the multiple bond is in the 1-position. Particularly preferred uracil derivatives which form part of the compounds as hereinbefore defined are 5-ethynyluracil and 5-propynyluracil. Other such inactivators include:

5-cyanouracil
5-bromoethynyluracil
5-(1-chlorovinyl) uracil
5-iodouracil
5-hex-1-ynyluracil
5-vinyluracil
5-trifluoromethyluracil
5-bromouracil Prodrugs of 5-fluorouracil are compounds which are metabolised in vivo to 5-fluorouracil and include 5-fluorouridine, 5-fluoro-2-deoxyuridine, 5-fluoro-2-deoxycytidine, 5'-deoxy-5-fluorouridine, 1-(2-tetrahydrofuranyl)-5-fluorouracil and 1-$C_{1-8}$ alkylcarbamoyl-5-fluorouracil derivatives.

Prodrugs of the uracil reductase inactivators are compounds which are metabolised in vivo to the corresponding uracil reductase inactivator.

Such prodrugs include nucleoside analogues which contain a nucleobase corresponding to the above 5-substituted uracil compounds. For example nucleoside derivatives containing a ribose, 2'-deoxy-ribose, arabinose or other cleavable sugar portion, which may contain a 2' or 3'-substituent such as halo, e.g. chloro or fluoro; alkoxy; amino or thio. Specific example of such nucleoside derivatives are 1-(6-O-arabinofuranosyl)-5-ethynyluracil and 1-(6-O-arabinofuranosyl)-5-prop-1-ynyluracil. Other uracil derivative prodrugs include 5-ethynyl-2-pyrimnidinone.

The nature of the linking group, L, should be such that the active components are released once the compound has been administered to the subject.

Thus, breakdown of a compound of the invention will result in release of both 5-fluorouracil and the uracil reductase inactivator, or prodrugs thereof.

In a preferred embodiment both the 5-fluorouracil moiety and the uracil reductase inactivator moiety are presented in the form of nucleosides, these then being linked such that upon administration to the subject the linkage breaks down releasing the active components.

Suitable sugar moieties which together with 5-fluorouracil and the uracil reductase inactivator can form such nucleosides include ribose, 2'-deoxyribose, arabinose and 5'-Cl-2'-deoxyribose.

Examples of suitable linking groups, L, include succinate groups, pyrophosphate groups, tartrate groups, mono-, di- or tri- phosphate groups and amide groups, with succinate and phosphate groups in general being particularly suitable.

Examples of preferred compounds of the invention include:

5-ethynyl-5"-fluoro-3',3'"-O-succinylbis-(1-(2-deoxy-β-D-erythropentofuranosyl) uracil);

5-ethynyluridine-5-fluoro-1-(β-D-arabinofuranosyl) uracil succinic acid 5', 2'-diester;

5-fluoro-5"-(1-propynyl)-2', 2'"-O-succinylbis(1-β-D-arabinofuranosyl uracil); and 5'-chloro-2'-5'-dideoxy-5-fluorouridine 2'"-deoxy-5"-ethynyluridine (3'-5'")diphosphate.

In general a suitable dose of a compound as hereinbefore described will be such as to provide a dose of 5-fluorouracil or a prodrug thereof in the range of 0.1 to 1000 mg per kilogram body weight of the recipient per day, preferably in the range of 0.1 to 200 mg per kilogram body weight per day. Most preferable is a dose in the range of 0.1 to 50 mg per kilogram body weight per day. For the uracil derivative component a suitable dose is in the range of 0.01 to 50 mg per kilogram body weight of the recipient per day, particularly 0.01 to 10 mg/kg. More preferably the dose should be such as to provide 0.01 to 0.4 mg per kilogram body weight per day as uracil derivative. Accordingly, a suitable dose of a compound as hereinbefore described will be in the range of 0.04 to 4000 mg per kilogram body weight per day, preferably in the range of 0.04 to 800 mg per kilogram body weight per day and most preferably in the range of 0.4 to 200 mg per kilogram body weight per day.

Given the nature of the compound it will be seen that it is possible, by including further linking groups, to increase the number of 5-fluorouracil moieties, or prodrugs thereof such that upon breakdown of the compound the dosages of 5-fluorouracil, or prodrug thereof, and uracil derivative fall within the abovementioned ranges.

Therefore the invention also provides compounds of the formulae (II) and (III):

X-(L-Y)n (II) and X-L-(Y)n (III)

Wherein X, L, and Y are as hereinbefore defined and n is at least 2. Preferably n is in the range 2–10.

For brevity, the term "a compound as hereinbefore defined" is used hereinafter to describe compounds of formula (I), (II) and (III).

In a further aspect the present invention provides a compound as hereinbefore defined for use in medicine, in particular for use in cancer chemotherapy.

In a still further aspect the present invention provides the use of a compound as hereinbefore defined in the manufacture of a medicament for use in cancer chemotherapy. The medicament may also be useful for the treatment of psoriasis, rheumatoid arthritis, or human papilloma virus infections.

In a further aspect the present invention provides a method for the treatment of cancer in a mammal comprising administering an effective amount of a compound as hereinbefore defined to said mammal. Alternatively, there is provided a method of reducing or inhibiting the tumour burden comprising administering to a mammal in need thereof an effective amount of a compound as hereinbefore defined.

In other aspects the invention further provides:

a) A method for the treatment or prophylaxis of psoriasis, rheumatoid arthritis or human papilloma virus infection which comprises administering an effective amount of a compound as hereinbefore defined to a mammal;

b) A method of reducing the toxicity and/or potentiating the efficacy and/or increasing the therapeutic index of 5-FU which comprises administering an effective amount of a compound as hereinbefore defined to a mammal;

c) A method of generating 5-ethynyluracil in a mammal which comprises administering a compound as hereinbefore defined wherein the uracil reductase inactivator is 5-ethynyluracil or a prodrug thereof, to a mammal; and d) A method of generating 5-fluorouracil in a mammal which comprises administering a compound as hereinbefore defined to a mammal.

Preferably the mammal is a human.

The required dose of the compound may be administered in unit dosage forms. The desired dose is preferably presented as one, two or more sub-doses administered at appropriate intervals. These sub-doses may be administered in unit dosage forms containing for example 1 to 200 mg of the compound.

The compound is preferably administered in the form of a pharmaceutical composition. Thus, in a further aspect the present invention provides a pharmaceutical composition comprising a compound as hereinbefore defined together with at least one pharmaceutically acceptable carrier or excipient, and optionally one or more other therapeutic ingredients.

Each carrier or excipient must be "pharmaceutically acceptable" in the sense of being compatible with the other ingredients of the composition and riot injurious to the patient. Compositions include those adapted for oral, rectal, nasal, topical (including buccal, transdermal and sublingual), vaginal and parenteral (including subcutaneous, intramuscular, intravenous and intradermal) administration. The compositions may conveniently be presented in unit dosage form and may be prepared by any methods well known in the art of pharmacy. Such methods include the step of bringing into association the active ingredient with the carrier which constitutes one or more accessory ingredients. In general, the compositions are prepared by uniformly and intimately bringing into association the active ingredient with liquid carriers or finely divided solid carriers or both, and then if necessary shaping the product.

Compositions of the present invention adapted for oral administration may be presented as discrete units such as capsules, sachets or tablets each containing a predetermined amount of the active ingredient; as a powder or granule; as a solution or a suspension in an aqueous or non-aqueous liquid; or as an oil-in-water liquid emulsion or a water-in-oil liquid emulsion. The active ingredient may also be presented as a bolus, electuary or paste. Oral administration is the preferred route.

A tablet may be made by compression or moulding, optionally with one or more accessory ingredients. Compressed tablets may be prepared by compressing in a suitable machine the active ingredient in a free flowing form such as a powder or granules, optionally mixed with a binder (e.g. povidone, gelatin, hydroxypropylmethyl cellulose), lubricant, inert diluent, preservative, disintegrant (e.g. sodium starch glycollate, cross-linked povidone, cross-linked sodium carboxymethyl cellulose) surface active or dispersing agent. Moulded tablets may be made by moulding in a suitable machine a mixture of the powdered compound moistened with an inert liquid diluent. The tablets may optionally be coated or scored and may be formulated so as to provide controlled release of the active ingredient therein using, for example, hydroxypropylmethyl cellulose in varying proportions to provide the desired release profile.

A capsule may be made by filling a loose or compressed powder on an appropriate filling machine, optionally with one or more additives. Examples of suitable additives include binders such as povidone; gelatin, lubricants, inert diluents and disintegrants as for tablets. Capsules may also be formulated to contain pellets or discrete sub-units to provide slow or controlled release of the active ingredient. This can be achieved by extruding and spheronising a wet mixture of the drug plus an extrusion aid (for example microcrystalline cellulose) plus a diluent such as lactose. The spheroids thus produced can be coated with a simipermeable membrane (for example ethyl cellulose, Eudragit WE30D) to produce sustained release properties.

Compositions for topical administration in the mouth include lozenges comprising the active ingredient in a flavoured base, usually sucrose and acacia or tragacanth; pastilies comprising the active ingredient in an inert base such as gellatin or glycerin, or sucrose and acacia; and mouthwashes comprising the active ingredient in a suitable liquid carrier.

Compositions for rectal administration may be presented as a suppository with a suitable base comprising for example cocoa butter or a salicylate.

Compositions for vaginal administration may be presented as pessaries, tampons creams, gels, pastes, foams or spray formulations containing in addition to the active ingredient such carriers as are known in the art to be appropriate.

Compositions for parenteral administration include aqueous and non-aqueous isotonic sterile injection solutions which may contain anti-oxidants, buffers, bacteriostats and solutes which render the composition isotonic with the blood of the intended recipient; and aqueous and non-aqueous sterile suspensions which may include suspending agents and thickening agents. The compositions may be presented in unit-dose or multidose sealed containers, for example, ampoules and vials, and may be stored in a freeze dried (lyophilized) condition requiring only the addition of the sterile liquid carrier, for example water for injections, immediately prior to use. Extemproaneous injection solutions and suspensions may be prepared from sterile powders, granules and tablets of the kind previously described.

Preferred unit dosage formulations are those containing a daily dose or unit, daily sub-dose, as hereinabove recited, or an appropriate fraction thereof, of an active ingredient.

Compounds of formula (I) are novel and accordingly a process for the preparation of these compounds provides a further aspect of the present invention.

Compounds of formula (1) may be prepared by reacting a uracil reductase inactivator or prodrug thereof, or a mono-protected derivative of a uracil reductase inactivator or prodrug thereof, with a compound L'-Y wherein Y is as hereinbefore defined or a protected derivative thereof and L' is a group capable of reacting with the uracil reductase inhibitor to form the linking group L, followed by deprotection where necessary. Suitable protecting groups will be known by one skilled in the art, and include tert-butyldimethylsilyl chloride, trimethylsilylacetylene or p-anisylchloro diphenylmethane(methoxytrityl).

The above coupling reaction may be carried out in a polar aprotic solvent, such as pyridine, in the presence of a coupling reagent, for example dicyclohexylcarbodiimide (DCC) or dimethylaminopyridine (DMAP). The reaction is carried out at a non-extreme temperature of −5° to 100° C., most suitably room temperature. Methods for the removal of the protecting groups may be carried out by methods known in the art, for example ion exchange using Dowex 50W-X8 [H⁺] in methanol can be used to remove the trityl groups (C. Malange, Chem. Ind. (1987) 856) and silyl protecting groups may be removed using tetraethyl ammonium fluoride in acetonitrile (S. Hanessian et al. Can. J. Chem. (1975) 53, 2975).

The group L' may be attached to the group Y by the reaction of a compound capable of creating a linking group with the compound Y in the presence of a suitable polar aprotic solvent, for example 1,3-dimethyl-3,4,5,6-tetrahydro-2(1H)-pyrimidinone (DMTHP). The reaction is carried out at a non-extreme temperature of −25° to 100° C., most suitably −5° C. to room temperature. Compounds capable of forming linking groups include succinic anhydride, phosphorous oxychloride. Such a process for the preparation of a compound of formula (I) wherein X and Y are both nucleoside prodrugs, may more clearly be understood by reference to Scheme 1.

To prepare compounds wherein X and Y are joined via a symmetrical linker, both X and Y may be reacted with a linking group, and the two resulting compounds combined to give a compound of formula (I) as described in Scheme 2 for the preparation of a compound of formula (I) wherein X and Y are both nucleoside prodrugs.

Intermediates of formula L'-Y are novel and accordingly provide a further aspect of the present invention.

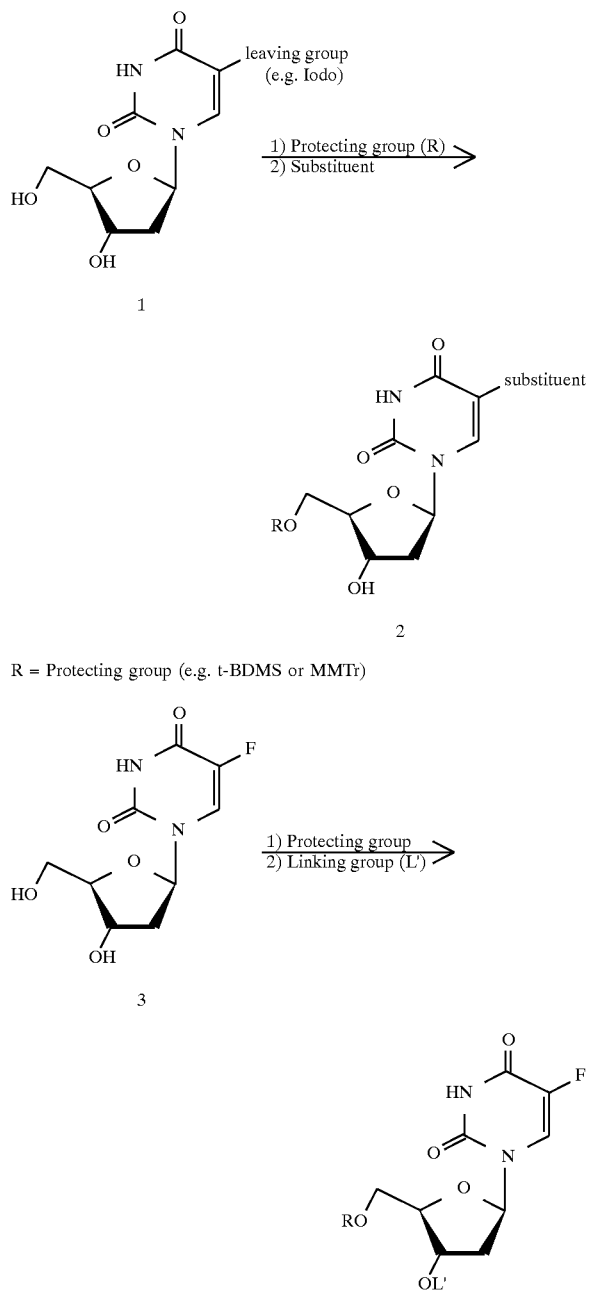

Scheme 1
(exemplified using, but not limited to nucleoside prodrugs)

R = Protecting group (e.g. t-BDMS or MMTr)

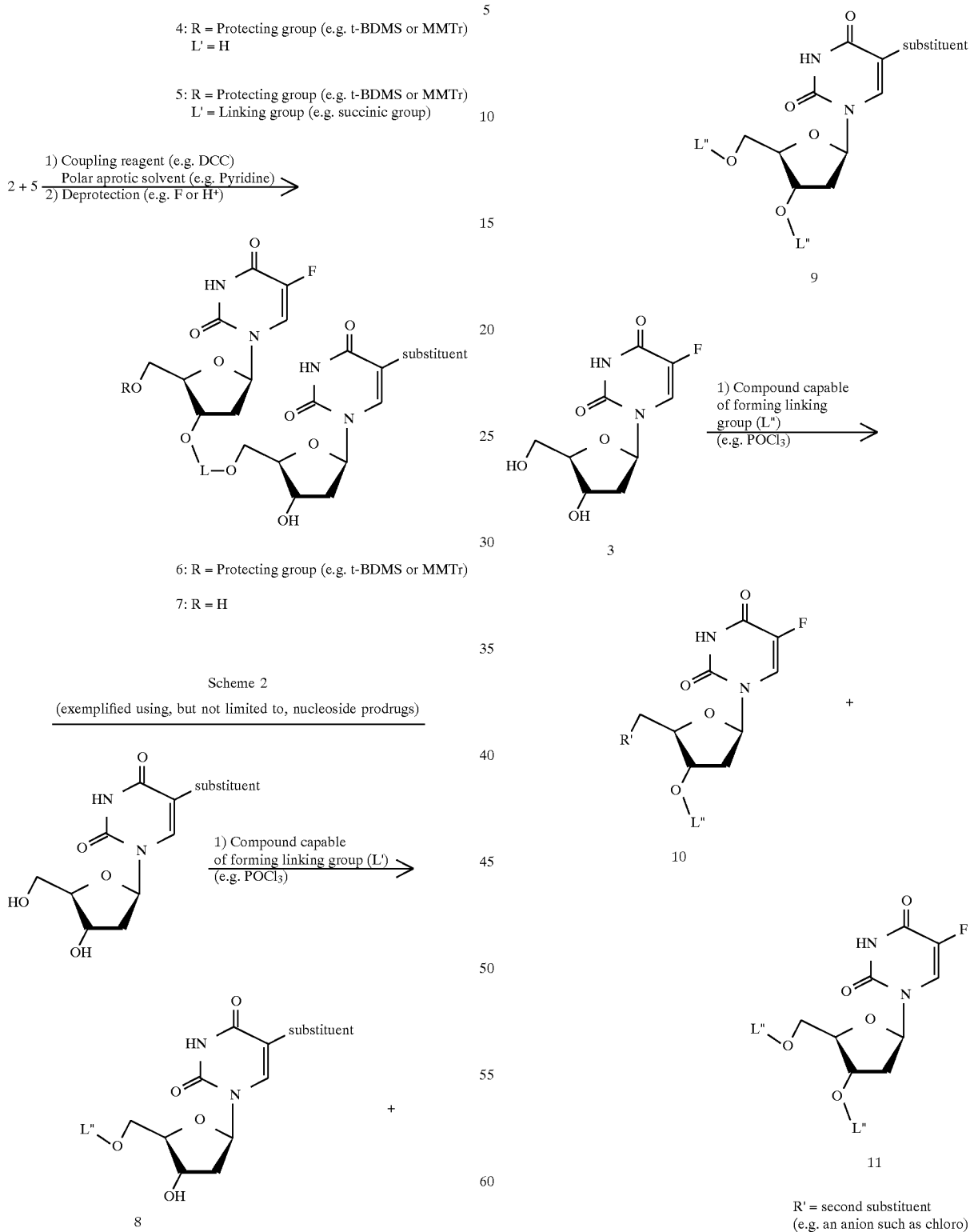

-continued
Scheme 2
(exemplified using, but not limited to, nucleoside prodrugs)

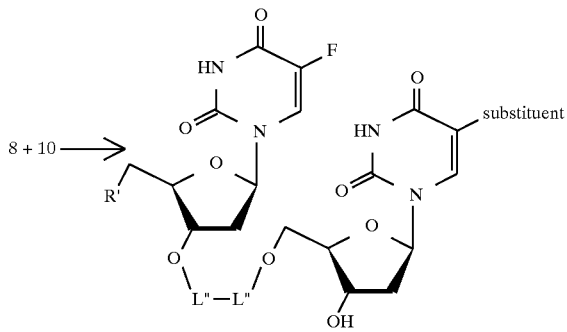

The invention will now be described with reference to, but not limited by, the following examples:

EXAMPLE 1

Preparation of 5-ethynyl-5"-fluoro-3,3"-O-succinylbis (1-(2-deoxy-β-D-erythropento furanosyl)uracil)

(a) 5'-O-(tert-Butyldimethylsilyl)-2'-deoxy-5-fluorouridine 5-Fluoro-2'-deoxyuridine (United States Biochemical Corporation, Cleveland, Ohio 44120) (6.00 g, 24.4 mmol) and 3.65 g (5.36 mmol) imidazole (Aldrich Chemical Company, Milwaukee, Wis. 53233) were dissolved in 25 ml anhydrous DMF in a flame dried round bottom flask. 4.0 g (26.8 mmol) of tert-Butyldimethylsilyl chloride (Aldrich) were added all at once, the flask was capped with a serum stopper and the solution was magnetically stirred over 3 days. After this time, 100 ml of saturated aqueous sodium bicarbonate was poured into the solution and the mixture was extracted with 2×200 ml ethyl acetate. The ethyl acetate layer was washed with 200 ml water, dried over magnesium sulphate and the solvent was removed on the rotary evaporator. The resulting residue was applied to a column (4.5×30 cm) packed with silica gel (350 g, 230–400 mesh) in dichloromethane. Under medium air pressure (9–12 psi) the column was first eluted with lL of 1% methanol in dichloromethane; successively eluted with 1 L of 1.5% methanol in dichloromethane, then 3 L of 2% methanol in dichloromethane and finally eluted with 3.5 L of 3% methanol in dichloromethane. Product fractions were pooled and the solvent evaporated to give 6.9 g (19.1 mmol) of the desired product as a white powder; Rf 0.34 (silica, 9:1 chloroform: methanol). $^1$H NMR (CDCl$_3$) δ8.85 (bs,1H, NH), 8.04 (d,1H, H6, J$_{F,H}$=6.4 Hz), 6.38-6.35 (dd overlapping, 1H, H1'), 4.50-4.46 (m, 1H, H3',) 4.08-4.06 (m, 1H, H4'), 3.97-3.92 (dd, 1H, H5, J=2.4 Hz, J=11.5 Hz), 3.86-3.81(dd, 1H, H5", J=2.0 Hz, J=11.4 Hz) 2.54-2.38 (m, 1H, H2"), 2.18-2.11(m,1H,H2"), 0.93 (s, 9H, tert-butyl), 0.15 (s, 6H, silyl methyls).

(b) 5'-O-(tert-Butyldimethylsilyl)-3'-O-(3-Carboxypropionyl)-2'-deoxy-5-fluorouridine 4.0 g (11.0 mmol) of 5'-O-(tert-Butyldimethylsilyl)-2'-deoxy-5-fluorouridine was dried by twice dissolving the nucleoside in 25 ml of anhydrous pyridine in a round bottom flask and evaporating the pyridine on a rotary evaporator. To the thus dried protected nucleoside re-dissolved in 20 ml pyridine was added 0.54 g (4.4 mmol) of 4-dimethylaminopyridine all at once and 0.84 g (8.4 mmol) succinic anhydride (Aldrich Chemical Company, Milwaukee, Wis. 53233) in three portions over 90 min. After stirring for 2.5 hrs, another equal portion of 4-dimethylaminopyridine was added. The flask was sealed with a serum stopper and the mixture was allowed to stir overnight. After this time, pyridine was removed on the rotary evaporator by co-evaporation with 4×50 ml toluene to give a tan foam. The foam was dissolved in 100 ml dichloromethane and extracted with 3×100 ml cold aqueous 10% citric acid, followed by 100 ml water. The dichloromethane layer was dried over magnesium sulphate, filtered, and the solvent was removed on a rotary evaporator to give 3.9 g of a tan foam. This foam was dissolved in a minimal amount of dichloromethane and applied to a column (4.5×30 cm) packed with silica gel (350 g, 230–400 mesh) in dichloromethane. Under medium air pressure (9–12 psi) the column was first eluted with 1 L of chloroform followed by elution with 1 L of 1% methanol in chloroform. The percentage of methanol was increased 1% for each successive litre. The product was eluted into fractions between 2% and 10% methanol in chloroform. Product fractions were pooled and the solvent was removed on the rotary evaporator to give 2.0 g (4.3 mmol) of a white solid: m.p. 133.4°–135.3° C.

(c) 5'-O-(tert-Butyldimethylsilyl)-2'-deoxy-5-iodouridine 5-Iodo-2'-deoxyuridine (United States Biochemical Corporation, Cleveland Ohio 44120) (10.0 g, 28.2 mmol) and 4.23 g (62.1 mmol) of imidazole (Aldrich Chemical Company, Milwaukee, Wis. 53233) were dissolved in 50 ml anhydrous dimethylformamide (DMF) in a flame-dried round bottom flask. 4.7 g (31.0 mmol) of tert-Butyldimethylsilylchloride (Aldrich) were added all at once; the flask was capped with a serum stopper and the solution was magnetically stirred for 11 days. After this period of time, the reaction mixture was poured into 300 ml aqueous saturated sodium bicarbonate and extracted with 4×150 ml ethyl acetate. The ethyl acetate extraction's were pooled, dried over magnesium sulphate, filtered and the solvent was removed on a rotary evaporator. The residue was applied to a column (4.5×30 cm) packed with silica gel (350 g, 230–400 mesh) in dichloromethane. Under medium air pressure (9–12 psi) the column was first eluted with 2 L of dichloromethane, followed by step-elution with 2 L of 1% methanol in dichloromethane, 2 L of 2% methanol in dichloromethane and finally 1 L of 3% methanol in dichloromethane. Pure product fraction were pooled and solvent removed on a rotary evaporator to give 8.8 g (18.8 mmol) of a white powder: Rf 0.30 (9:1 chloroform: methanol). $^1$H NMR (300 MHz, CDCl$_3$) δ8.30-8.20 (bs,1H, NH), 8.10 (s,1H, H6), 6.32-6.27 (dd overlapping, 1H, H1') 4.49-4.46 (m, 1H, H3'), 4.10-4.07 (m,1H, H4'), 3.94-3.89 (dd, 1H, H5", J$_{5",5'}$=11.5 Hz, J$_{5",4'}$=2.6 Hz), 3.85-3.81 (dd, 1H, H5', J$_{5',5"}$=11.5 Hz, J$_{5',4'}$=2.3 Hz), 2.45-2.42 (m, 1H, H2"), 2.41-2.38 (m, 1H,H2'), 0.96 (S,9H, tert-butyl), 0.93 (s, 3H, silyl methyl), 0.92 (s, 3H, silyl methyl).

(d) 1-(5-O-(tert-Butyldimethylsilyl)-2-deoxy-β-D-erythro-pentofuranosyl-5-(2-(trimethylsilyl)ethynyl)uracil)

To a solution of 5.0 g (10.7 mmol) of 5'-O-(tert-butyldimethylsilyl)-2'-deoxy-5-iodouridine, 0.62 g (3.3 mmol) copper (I) iodide, and 3.3 g (4.6 ml, 32.8 mmol) triethylamine in 50 ml dimethylformamide (DMF) under a nitrogen atmosphere was added 4.8 g (7.0 ml, 49.3 mmol) of trimethylsilylacetylene and 1.9 g (1.6 mmol) of tetrakis (triphenylphosphine)palladium(0) (Aldrich Chemical Company, Milwaukee, Wis. 53233). The dark mixture was magnetically stirred at room temperature overnight. DMF was removed in vacuo on a rotary evaporator and the dark oily residue was dissolved in 100 ml chloroform and extracted with 2×150 ml of aqueous 5% ethylenediamine tetra acetic acid disodium salt, followed by 1×150 ml water.

The chloroform layer was dried over magnesium sulphate, filtered and the solvent removed on a rotary evaporator. The residue was dissolved in a minimal amount of chloroform and applied to a column (4.5×30 cm) packed with silica gel (350 g, 230–400 mesh) in chloroform. Under medium air pressure (9–12 psi) the column was eluted with 2 L of chloroform followed by 3.5 L of 1% methanol in chloroform to elute the desired product. After removal of the solvent on a rotary evaporator, 2.7 g (6.2 mmol) of product was obtained as a tan solid: Rf 0.51 (silica, 9:1 chloroform: methanol). $^1$H NMR (300 MHz, CDCl$_3$) δ8.15-8.10(bs,1H, NH),7.97 (s,1H, H6), 6.34-6.29 (dd overlapping, 1H, H1'), 4.51-4.48 (m, 1H, H3') 4.10-4.08 (m, 1H, H4'), 3.95-3.90 (dd,1H, H5", $J_{5'',5'}$=11.4 Hz, $J_{5'',4'}$=2.6 Hz), 3.85-3.80 (dd 1H, H5', $J_{5',5''}$=11.4 Hz, $J_{5',4'}$=2.1 Hz), 2.41-2.37 (m, 1H H2"), 2.16-2.11 (m, 1H H2"), 1.86 (s, 9H, C(CH$_3$)$_3$), 0.20 (s, 9H, acetylenic Si(CH$_3$)$_3$), 0.15 (s, 3, Silyl methyl), 0.13 (s, 3H, silylmethyl).

(e) 5-Fluoro-5"-(2-(trimethylsilyl)ethynyl-3',3"'-O-succinylbis-(1-(2-deoxy-5-O-(tert-butyldimethylsilyl)-β-D-erythro-pentofuranosyl)uracil)

In a previously flame dried round bottom flask was dissolved 0.51 g (1.1 mmol) of 1-(5-O-(tert-butyldimethylsilyl)-2-deoxy-β-D-erythro-pentofuranosyl-5-(2-(tri methylsilyl)ethynyl)uracil and 0.49 g (1.1 mmol) of 5'-O-(tert-butyldimethylsilyl)-3'-O-(3'-carboxypropionyl)-2'-deoxy-5-fluorouridine in 5 ml anhydrous pyridine. To this solution was added 0.46 g (2.2 mmol of dicyclohexylcarbodiimide (Aldrich Chemical Company, Milwaukee, Wis. 53233) and the solution was allowed to magnetically stir overnight. The following day, pyridine was removed on the rotary evaporator and the orange-brown syrup was resuspended in ice-cold ethyl acetate. Dicyclohexylurea was removed by vacuum filtration and the ethyl acetate was subsequently removed on the rotary evaporator. The residue was re-dissolved in a minimal amount of dichloromethane and applied to a column (4.5×30 cm) packed with silica gel (350 g, 230–400 mesh) in dichloromethane. Under medium air pressure (9–12 psi) the column was eluted with 2 L of dichloromethane followed by 4 L of 1.5% methanol in dichloromethane for elution of an impure product. The product was re-chromatographed across 100 g silica packed in hexanes under medium air pressure and eluted by an increasing step-gradient from 5 to 50% ethyl acetate in hexanes. After removal of solvent on a rotary evaporator, 0.60 g (0.68 mmol) of the product was obtained as a white powder: R$_f$0.54 (silica, 9:1 chloroform: methanol); m.p. 139.8° C., resolidifies to melt at 208°–210° C.

(f) 5-Ethynyl-5"-fluoro-3',3"-O-succinylbis-(1-(2-deoxy-β-D-erythro-pentofuranosyl)uracil)

0.90 g (1.0 mmol) of 5-Fluoro-5"-(2-trimethylsilyl)ethynyl-3',3'"-O-succinylbis (1-(2-deoxy-5-O-(tert-butyldimethylsilyl)-beta-D-erythro-pentofuranosyl)uracil) was treated with 3.3 equivalents of tetraethyl ammonium fluoride hydrate (Aldrich Chemical Company, Milwaukee, Wis. 53233) in 25 ml acetonitrile and allowed to magnetically stir at ambient temperature overnight.

The following day, an additional equivalent of the fluoride reagent was added and the solution was allowed to stir for several more hours. The solution was then directly applied to a 100 g silica gel (230–400 mesh) column (2.5×30 cm) packed in dichloromethane. The column was eluted with 500 ml of dichloromethane, followed by a step-gradient of 1 to 5% methanol in dichloromethane. Overnight, the fractions precipitated out of the 5% methanol fractions to give 156 mg of analytically pure product after filtration and drying. The combined mother liquors were combined and evaporated to give an additional 270 mg of product after drying for a total of 0.426 g (0.73 mmol): m.p. 229.5°–230.6° C. $^1$H NMR (DMSO-d$_6$) δ11.9-11.6 (bs, 2H, N3H & N3"H), 8.29 (s, 1H, H6), 8.21 (d, 1H, H6", $J_{F,H}$=7.1 Hz), 6.16-6.12 (m, 2H, H1' & H1'"), 5.33-5.30 (m, 2H, H3' & H3'"), 5.29-5.24 (m, 2H, 5'OH & 5'"OH), 4.14 (s, 1H, acetylenic H), 4.04-4.01 (m, 2H, H4' & H4'"), 3.65-3.63 (m, 4H<H5' & H5'"), 2.65 (s, 4H, succinate), 2.33-2.26(m, 4H, H2' & H2'").

EXAMPLE 2

Preparation of 5-ethynyl-5"-fluoro-3',3"-O-succinylbis(1-(2-deoxy-β-D-erythropento furanosyl) uracil)

(a) 2'-Deoxy-5-fluoro-5'-O-(4-methoxytrityl)uridine

5-Fluoro-2'-deoxyuridine (United States Biochemical Corporation, Cleveland, Ohio 44120) (1.0 g, 4.1 mmol) was twice suspended in 30 ml anhydrous pyridine in a round bottom flask and the pyridine removed on a rotary evaporator at 50° C. and oil pump vacuum. The deoxyribonucleoside thus dried was re-dissolved in 41 ml pyridine and cooled to ca. 5° C. in an ice-water bath. The solution was magnetically stirred. To the solution was added 0.06 equivalents (30 mg, 0.24 mmol) 4-dimethylaminopyridine and 1.4 equivalents triethylamine (0.8 ml, 5.7 mmol) all at once. This was followed by the addition of 1.2 equivalents (1.5 g, 4.9 mmol) p-anisylchlorodiphenylmethane (Aldrich Chemical Company, Milwaukee, Wis. 53233) in one-quarter portions every 45 min. After the final addition of p-anisylchlorodiphenylmethane, the ice-bath was allowed to gradually warm to ambient temperature. The reaction was sealed with a serum stopper and magnetically stirred overnight. After this period an additional 350 mg of p-anisylchlorodiphenylmethane was added and the reaction was allowed to stir for another 8 hrs. The reaction was then poured into 100 ml water in a separating funnel and extracted with 4×100 ml diethyl ether. Diethyl ether was removed on a rotary evaporator. 2.4 g of crude material was dissolved in a minimal amount of dichloromethane and applied to a column (2.5×30 cm) packed with silica gel (100 g, 230–400 mesh) in dichloromethane. Under medium air pressure (9–12 psi) the column was first eluted with 2 L of dichloromethane followed by 1 L of 3% methanol in dichloromethane to elute the product. After evaporation of solvent, the product was obtained as a white foam (1.8 g, 3.2 mmol): Rf 0.42 (silica, 9:1 chloroform: methanol). $^1$H NMR (300 MHz, DMSO-d$_6$) δ 11.87 (s, 1H, NH) 7.88 (d, 1H, H6, $J_F$, H=6.85 Hz), 7.42-7.23 (m, 10H, Ar H), 6.90 (d, 2H, Ar H, J=8.89 Hz), 6.14-6.12 (overlapping dd, 1H, H2'), 5.34 (d, 1H, 3'OH, J=4.57 Hz), 4.27 (m, 1H, H3'), 3.88 (m,1H,H4') 3.75 (s, 3H, OCH$_3$) 3.34-3.25 (m, 1H, H5'), 3.16-3.12 (m, 1H, H5"), 2.26-2.16 (m, 2H, H2" & H2').

(b) 2'-Deoxy-5-iodo-5'-O-(4-Methoxytrityl)uridine

5-Iodo-2'-deoxyuridine (United States Biochemical Corporation, Cleveland, Ohio 44120) (1.0 g, 2.8 mmol) was twice suspended in 30 ml anhydrous pyridine in a round bottom flask and the pyridine removed on a rotary evaporator at 50° C. and oil pump vacuum. The deoxynucleoside thus dried was re-dissolved in 28 ml pyridine and cooled to ca 5° C. in an ice-water bath. The solution was magnetically stirred. To the solution was added 0.06 equivalents (20 mg, 0.16 mmol) 4-dimethylaminopyridine and 1.4 equivalents (0.55 ml, 4.0 mmol) triethylamine all at once followed by the addition of 1.2 equivalents (1.0 g, 3.4 mmol) of p-anisylchlorodiphenylmethane (Aldrich Chemical Company, Milwaukee, Wis. 53233) in one-quarter portions every 45 min. After the addition of the final portion of p-anisylchlorodiphenylmethane, the ice bath was allowed to gradually warm to ambient temperature. The reaction was sealed with a serum stopper and magnetically stirred overnight. After this period, an additional 250 mg of p-anisylchlorodiphenyl methane was added and the reaction was allowed to stir for an additional 8 hrs. The reaction was then poured into 100 ml water in a separating funnel and extracted with 4×100 ml diethyl ether. The diethyl ether extracts were cooled and the solvent was removed on a rotary evaporator. 2.4 g of crude material was dissolved in a minimal amount of dichloromethane and applied to a column (2.5×30 cm) packed with silica gel (100 g, 230–400 mesh in dichloromethane). Under medium air pressure (9–12 psi), the column was first eluted with 1 L of dichloromethane, then with 1 L of 1% methanol in dichloromethane and finally with 1 L of 5% methanol in dichloromethane to elute the product. After evaporation of solvent, the product was obtained as an off-white foam (1.3 g, 1.9 mmol): $R_f$ 0.48 (silica, 9:1 chloroform:methanol). $^1$H NMR (300 MHz, DMSO-d$_6$) δ 11.75 (s, 1H, NH), 8.02 (s, 1H, H6), 7.43-7.23 (m, 10H, Ar H), 6.91 (d, 2H, Ar H, J=8.89 Hz), 6.13-6.08 (overlapping dd, 1H, H1'), 5.32 (d,1H, 3'OH, J=4.57 Hz) 4.24 (m, 1H, H3'), 3.91 (m, 1H, H4'), 3.75 (s,3H,OCH$_3$), 3.34-3.17 (m, 2H, H5' & H5"), 2.26-2.17 (m, 2H, H2" & H2).

(c) 2'-Deoxy-5-ethynyl-5'-O-(4-methoxytrityl)uridine

2'-Deoxy-5-iodo-5'-O-(4-methoxytrityl)uridine (1.2 g, 1.8 mmol) was dissolved in 6 ml of anhydrous N,N-dimethylformamide (DMF) and the solution was vigorously deoxygenated with nitrogen for 30 min. To the magnetically stirred solution was added 142 mg (0.20 mmol) bis (triphenylphosphine)palladium(II) chloride, 76 mg (0.40 mmol) copper (I) iodide, 0.53 ml (5.40 mmol) of trimethylsilylacetylene and 0.56 ml (4.0 mmol) of triethylamine (Aldrich Chemical Company, Milwaukee, Wis. 53233). The following day identical portions of bis(triphenylphosphine) palladium(II)chloride, copper (I) iodide, trimethylsilylacetylene and triethylamine were added. The reaction was allowed to stir for an additional 5 hrs before being poured into 100 ml ethyl acetate in a separating funnel. The ethyl acetate solution was extracted with 3×30 ml aqueous 5% ethylenediamine tetra acetic acid disodium salt and washed with 1×30 ml water. Ethyl acetate was removed on the rotary evaporator to give a black foam. This foam was dissolved in 5 ml of acetonitrile and 222 mg (1.5 mmol) of tetraethyl ammonium fluoride hydrate (Aldrich Chemical Company, Milwaukee, Wis. 53233) was added and the solution was magnetically stirred for 1 hr. After this period the reaction mixture was loaded directly onto a column (2.5 C 30 cm) packed with silica gel (100 g, 230–400 mesh) in chloroform. Under medium air pressure (9–12 psi) the column was first eluted with 1 L of chloroform, then 1 L of 1% methanol in chloroform and finally with 1 L of 2.5% methanol in chloroform to elute the product. The appropriate product fractions were combined and solvent was removed on a rotary evaporator to 769 mg (1.5 mmol) of a light brown foam: Rf 0.23 (silica, 95:5 chloroform: methanol) ; IR (1% KBr) acetylenic carbon-carbon stretch 2110 cm$^{-1}$; MS (EI, Cl,) 524 (M). $^1$H NMR (300 MHz, DMSO - d$_6$) δ 11.69 (s, 1H, NH), 7.94 (s, 1H, H6), 7.41-7.21 (m, 10H, Ar H), 6.90 (d, 2H, Ar H, J=8.9 Hz), 6.11-6.07 (overlapping dd, 1H, H1'), 5.30 (d, 1H, 3' OH, J=4.6 Hz), 4.24 (m, 1H, H4'), 3.74 (s, 3H OCH$_3$), 3.41-3.11 (m, overlapping water peak, H5' & H5"), 2.27-2.18 (m, 2H, H2" & H2').

(d) 5-Ethynyl-5"-fluoro-3',3'"-O-succinylbis(1-(2-deoxy-5-O-(4-methoxytrityl)-β-D-erythro-pentofuranosyl)uracil)

To a 50 ml flame dried round bottom flask with magnetic stir bar was added 726 mg (1.3 mmol) of 2'-deoxy-5-fluoro-5'-O-(4-methoxytrityl)uridine, 32 mg (0.26 mmol) of 4-dimethylaminopyridine (DMAP) and 143 mg (1.4 mmol) of succinic anhydride. The mixture was dissolved in 6 ml of pyridine sealed under a septum and magnetically stirred overnight. The following day an additional 30 mg of DMAP and 30 mg of succinic anhydride was added and the reaction was stirred for an additional 24 h. On the third day, 1.05 g (5.1 mmol) of 2'-deoxy-5-ethynyl-5'-O-(4-methoxytrityl) uridine was added and the mixture was allowed to stir overnight. The following day, dicyclohexylurea was removed via suction filtration through a sintered glass funnel and was washed with ethyl acetate. The filtrate was partitioned between ethyl acetate and water. The ethyl acetate layer was dried over magnesium sulphate, filtered and evaporated on a rotary evaporator. The title compound was obtained by successive medium air pressure (9–12 psi) silica gel (100 g, 230–400 mesh) column (2.5×30 cm) chromatography eluting with dichloromethane, followed by 1% then 3% methanol in chloroform. After evaporation of solvent, the product was obtained as a white foam (0.27 g, 0.22 mmol): Rf 0.35 (silica, 9:1 chloroform: methanol). $^1$H NMR (300 MHz, DMSO-d$_6$) δ 12.00-11.68 (2 bs 2H, N3H & N3"H), 7.97 (s, 1H, H6), 7.89 (d, 1H, H"6, $J_{F,H}$=6.8 Hz), 7.40-7.20 (m, 10H, Ar H), 6.88 (d, 2H, ArH, J=8.8 Hz), 6.18-6,10 (m. 2H, H1' & H1'") 5.25-5.23 (m, 2H, H3' & H3'"), 4.07 (m 2H, H4' & H4'"), 4.00 (s, 6H, 2 X OCH$_3$), 3.20-3.40 (m, obscured by water, H5' & H5'") 2.40 (s, 4H, succinate), 2.50-2.20 (m, 4H, H2' & H2'").

(e) 5-Ethynyl-5"-fluoro-3',3'"-O-succinylbis(1-(2-deoxy-β-D-erythro-pentofuranosyl)uracil)

0.130 g (0.11 mmol) of 5-Ethynyl-5"-fluoro-3',3'"-O-succinylbis(1-(2-deoxy-5-O-(4-methoxytrityl)-β-D-erythropentofuranosyl)uracil) was dissolved in 10 ml of anhydrous methanol in a round bottom flask. 400 mg of methanol-washed Dowex-50WX8 (H$^+$ form, 20–50 mesh, J. T. Baker) was added and the mixture warmed to 55° C. for 4 h. The solution was filtered to remove the resin and the beads washed with methanol. The filtrate was rotary evaporated to dryness. The off-white solid was suspended in dichloromethane and collected by suction-filtration, washed with dichloromethane then water and dried in a vacuum oven overnight at 50° C. 0.035 g (0.059 mmol) of an off-white solid was obtained. $^1$H NMR (300 MHz, DMSO-d$_6$) δ 12.0 (bs, 2H, N3H & N3"H), 8.29 (s, 1H, H6), 8.21 (d, 1H, H"6, $J_{F,H}$=7.1 Hz), 6.16-6.12 (m, 2H. H1' & H1'"), 5.35-5.30 (m, 2H, H3' & H3'"), 5.59-5.24 (m, 2H,5'OH & 5'"OH), 4.14 (s, 1H, acetylenic H), 4.04-4.01 (m, 2H, H4' & H4'"), 3.65-3.63 (m, 4H, H5' & H5'"), 2.65 (s, 4H, succinate), 2.33-2.26 (m, 4H, H2' & H2'").

EXAMPLE 3

Preparation of 5'-chloro-2',5'-Dideoxy-5-Dideoxy-5-fluorouridine 2'"-Deoxy-5"-Ethynyluridine(3'-5'") Diphosphate (a) 2'-Deoxy-5-(2-(Trimethylsilyl)Ethynyl)Uridine The title compound was prepared according to the procedure of Morris J. Robbins and Philip J Barr, *J.Org. Chem.*, 1983, 48, 1854–1862.

A mixture of 5-iodo-2'-deoxyuridine (U.S. Biochemical Corp., Cleveland, Ohio) (2.7 mmol), dimethylformamide (8 ml), and triethylamine (0.6 ml) was deoxygenated with a rapid stream of N$_2$ over 10 min in a flame dried 100 ml round-bottom flask with magnetic stirring. To this deoxygenated solution was added copper iodide (Aldrich Chemical Co., Milwaukee, Wis.) (1.0 mmol), bis (triphenylphosphine)palladium(II)chloride (Aldrich) (0.5 mmol), and (trimethyl silyl)acetylene (Aldrich) (5.4 mmol). The mixture was allowed to magnetically stir at room temperature overnight, at which time there was no starting nucleoside as evidenced by TLC (Silica, 9:1 chloroform:methanol). DMF was removed on a vacuum pump at ambient temperature. The crude material was applied in chloroform to a 70 g silica gel (230–400 mesh) column (2.5×30 cm) packed in 3% methanol in chloroform. Under medium air pressure (9–12 psi), the column was eluted with 1 L of 3% methanol in chloroform. and then 1 L of 5% methanol in chloroform. 100 ml fractions were collected. Fractions 10–15 contained the desired product. The product fractions were pooled and solvent was removed on a rotary evaporator to give the product as a hygroscopic yellow foam (2.3 mmol, 85% yield): $R_f$ 0.15 (silica, 9:1 chloroform: methanol). 1 R (KBr) 2167 cm$^{-1}$, acetylenic C≡C stretch. $^1$H NMR (300 MHz, DMSO-d6) δ 11.7-11.6 (bs, 1H, N-H), 8.26 (s,1H,H-6), 6.11-6.07 (t, 1H, H1', J=6.5 Hz), 5.26-5.24 (d, 1H, 3'-OH, J=4.3 Hz), 5.13-5.09 (t, 1H, 5'-OH, J=5.0 Hz), 4.25-4.20 (m - 5 Lines, 1H, H3'), 3.80-3.76 (q, 1H, H4'), 3.63-3.55 (m, 2H, H5" and H5' overlapping), 2.16-2.10 (m, 2H, H2" and H2'), 0.20 (s, 9H, Si(CH$_3$)$_3$).

(b) 2'-Deoxy-5-Ethynyluridine

The title compound was prepared according to a modification of the procedure of Morris J. Robbins and Philip J Barr, *J. Org. Chem.*, 1983, 48, 1854–1862.

A mixture of 2'-deoxy-5-(2-(trimethylsilyl)ethynyl) uridine (2.4 mmol) and tetraethyl ammonium fluoride hydrate (Aldrich Chemical Co., Milwaukee, Wis.) (2.4 mmol) was magnetically stirred in 10 ml dry acetonitrile (Aldrich) for 1 hour. The solution was applied directly to a column (2.5×30 cm) of 100 g silica gel (230–400 mesh) packed in dichloromethane. The column was eluted with 3% methanol in dichloromethane to obtain pure product (1.7 mmol, 71% yield) as an off-white solid after evaporation of solvent. 1R (KBr) 2120 cm$^{-1}$, C≡C stretch. $^1$H NMR (300 MHz, DMSO-d6) δ 11.58-11.65 (bs, 1H, NH), 8.30 (s, 1H,H6), 6.13-6.08 (t, 1H, H1', J=6.55 Hz), 5.26-5.24 (d, 1H, 3'-OH, J=4.3 Hz), 5.15-5.12 (t, 1H, 5'-OH, J=4.90 Hz), 4.26-4.21 (m - 5 lines, 1H, H3'), 4.11 (s, 1h, acetylenic H), 3.82-3.79 (q, 1H, H4'), 3.63-3.56 (m, 2H, H5" and H5'), 2.15-2.12 (m, 2H, H2" and H2').

(c) 1-(2-Deoxy-β-D-Erythro-Pentofuranosyl)-5-Ethynyluracil 5'-Monophosphate and 1-(2-Deoxy-β-D-Erythro-Pentofuranosyl)-5-Ethynyluracil 3',5'-Diphosphate 2'-Deoxy-5-ethynyluridine (1.7 mmol) was co-evaporated several times in a 25 ml round-bottom flask with dry acetonitrile (Aldrich Chemical Co., Milwaukee, Wis.). The nucleoside was dissolved in 5 ml of 1,3-dimethyl-3,4,5,6-tetrahydro-2(1H)-pyrimidinone (Aldrich) with magnetic stirring. The flask was sealed with a serum stopper and the-solution stirred in a methanol-ice bath at −12° C. for 5 minutes. 3 equivalents (0.4 ml) of phosphorous oxychloride (Aldrich) from a freshly opened ampoule was added to the nucleoside solution. After 5 min reaction time, the mixture was quenched with 5 ml of water with continued stirring. After 3 min, 0.5 ml of tributylamine (Aldrich) was added. The product mixture was diluted with water and loaded onto 80 g of DEAE Sephadex swollen in 50 mM ammonium bicarbonate. The column was eluted with an increasing gradient of aqueous ammonium bicarbonate (50 mM to 500 mM) with UV detection at 280 mm. Elution flowrate was as controlled by Gilson Minipuls 2 peristaltic pumps (Gilson, Middleton, Wis.). The first eluting product fractions were pooled and evaporated on a rotary evaporator at 45° C. The resulting white solid was co-evaporated multiple times with water on the rotary evaporator, then re-dissolved in 15 ml of water, frozen and lyophilised to give 0.34 mmol (20% yield) of the 5'-monophosphate as a white monoammonium salt. HPLC was performed on a 4.6 mm X 100 mm, 5 micron, analytical strong anion exchange column (Alltech, Deerfield, Ill.) with a linear gradient of 10 mM to 1M ammonium phosphate, pH 5.5, 5% methanol over 30 min. This product had a retention time ($R_t$) of 3.4 minutes. Negative Ion FAB MS (dithioerythritol/dithiothreitol) (M-H)$^-$=331.1. $^{31}$P NMR (121. 421 MHz, $^1$H decoupled, 85% phosphoric acid δ=0.0, DMSO-d6) δ 0.32 (s, 1P, 5'phosphate). 'H NMR (300 MHz$_2$, DMSO-d6) δ 7.97 (s, 1H, H6), 6.09-6.05 (overlapping dd, 1H, H1'), 4.27-4.25 (bs, 1H, H3'), 4.05 (s, 1H, acetylenic H) 3.89-3.85 (bs, 1H, H4'), 3.79-3.76 (m, 2H, H5" and H5') 2.15-2.05 (H2" and H2').

A second product eluted after the 5'-monophosphate. Identical fractions were pooled, evaporated and lyophilised as before to give 0.62 mmol (37% yield) of the 3',5'-diphosphate of the starting nucleoside. Analytical HPLC (as above), $R_t$=8.0 min. Negative Ion FAB MS (dithioerythritol/dithiothreitol) (M-H)$^-$=411.0. $^{31}$P NMR (121.421 MHz, $^1$H decoupled, 85% phosphoric acid δ=0.0, DMSO-d6) δ −0.01 (s, 1P,5' phosphate), −1.07 (s, 1P, 3' phosphate). $^1$H NMR (300 MHz, DMSO-d6) δ 8.00 (S, 1H, H6), 6.10-6.05 (t, 1H, H1', J=7.1 Hz), 4.76-4.74 (m - broad, 1H, H3'), 4.17-4.16 (s, 1H, H4'), 4.06 (s,1H, acetylenic H), 3.90-3.78 (2 multiplets, 2H, H5" and H5'), 2.22-2.21 (m - broad, 2H, H2" and H2').

The 5'-monophosphate and the 3',5-diphosphate were assayed for ammonia according to the assay of A. L. Chaney and E. P. Marbach, *Clin. Chem.* 1962, 8, 130–132. The phosphates were assayed for phosphorous according to procedure of B. N. Ames, *Methods Enzymol.* 1966, 8, 115–118.

(d) Preparation of 1-(2-Deoxy-β-D-Erythro-Pentofuranosyl)-5-Ethynyluracil 5'-Monophosphate From 1-(2-Deoxy-β-D-Erythro-Pentofuranosyl)-5-Ethynyl uracil 3',5'-Diphosphate By Enzymatic Dephosphorylation With Nuclease P1

To 1-(2-deoxy-β-D-erythro-pentofuranosyl)-5-ethynyluracil 3',5'-diphosphate (0.50 mmoles) in 5 ml of water was added 50 microliters of aqueous 1M ZnCl$_2$ and 250 microliters of a 30 mM sodium acetate buffer, pH 5.0, containing 1 unit of Nuclease P1 (from Penicillium citrinum, Boehringer Mannheim, Indianapolis, Ind.) per microliter. The mixture was heated in a water bath at 50° C. for 3 hours. The product was purified and characterised as previously described. The yield was quantitative.

(e) 5'-Chloro-2',5'-Dideoxy-5-Fluorouridine 3'-O-Phosphate and 2'-Deoxy-5-Fluoro uridine 3',5'-Di-O-Phosphate This is a modification of the procedure found in European Patent Application No. 910502.6; Inventor, S. M. Tisdale et al.; Title, *Antiviral Compounds.* and Bull.Chem.Soc.Japan (1969), 42, 350.

2'-Deoxy-5-fluorouridine (4.1 mmol) (United States Biochemical, Cleveland, Ohio was dissolved in 7 ml of 1,3-dimethyl-3,4,5,6-tetrahydro-2(1H)-pyrimidinone (Aldrich) in a vial equipped with a magnetic stir bar and cap. The vial was cooled to −5° C. in an ice-methanol bath. 1.5 ml of phosphorous oxychloride was added to the stirring solution and the solution continued to stir in the bath for 7 min. The reaction was then quenched by the addition of 5 ml of water, and the mixture was allowed to stir in the cold bath for 5 min. The mixture was poured into 30 ml of tributylamine, diluted with 900 ml water and loaded onto 80 g of DEAE Sephadex swollen in 50 mM ammonium bicarbonate. The column was eluted with an increasing gradient of aqueous ammonium bicarbonate (50 mM to 500 mM) with UV detection at 267 nm. Elution flowrate was controlled by Gilson Minipuls 2 peristaltic pumps (Gilson, Middleton, Wis.). The first eluting product fractions were pooled and evaporated on a rotary evaporator at 45° C. The resulting white solid was co-evaporated multiple times with water on the rotary evaporator, then re-dissolved in 15 ml of water, frozen and lyophilised to give 1.2 mmol (29% yield) of the 5'-chloro-2',5'-dideoxy-5-fluorouridine 3'-O-phosphate as the mono-ammonium salt. HPLC was performed on a 4.6 mm×100 mm, 5 micron, analytical strong anion exchange column (Alltech, Deerfield, Ill.) with a linear gradient of 10 mM to 1M ammonium phosphate, pH 5.5, 5% methanol over 30 min. Ths product had a retention ($R_t$ of 3.6 minutes. Positive Ion FAB MS (glycerol) (M+1)$^+$=345.1. $^{31}$P NMR (121. 421 MHz, $^1$H decoupled, 85% phosphoric acid δ =0.0, DMSO-d6) 67 −0.56 (s, 1P, 3'-phosphate). $^1$H NMR (300 MHz, DMSO-d6) δ 7.96-7.94 (d, 1H, H6, J=7.0 Hz), 6.15-6.13 (triplet - broadened, 1H, H1'), 4.56-4.54 (bs, 1H, H3'), 4.17-4.16 (bs, 1H, H4'), 3.95-3.90 (overlapping multiplets, 2H, H5 " and H5', 2.39-2.19 (m, 2H, H2" and H2').

A second product eluted after the 5'-monophosphate. Identical fractions were pooled, evaporated and lyophilised as before to give 0.62 mmol (37% yield) of the 3',5'-diphosphate of the starting nucleoside. Analytical HPLC (as above), $R_t$=8.5 min. Positive Ion FAB MS (glycerol) (M+1)$^+$=407.4. $^{31}$P NMR (121.421 MHz, $^1$H decoupled, 85% phosphoric acid δ=0.0, DMSO-d6) 67 −0.369 (s, 1P,5'phosphate), −1.45 (s, (1P, 3' phosphate). $^1$H NMR (300 MHz, DMSO-d6) δ 8.12-8.10 (d, 1H, H6, J=7.0 Hz), 6.12-6.10 (t, 1H, H1'), 4.82-4.79 (m, 1H, H3'), 2.23-2.20 (m, 2H, H2" and H2').

The phosphates were assayed for phosphorous according to procedure of B. N. Ames, *Methods Enzymol.* 1966, 8, 115–118.

(f) 5'-Chloro-2',5'-Dideoxy-5-Fluorouridine 2'''-Deoxy-5"-Ethynyluridine (3',5''') Diphosphate This phosphoimidazolidate procedure is based on the synthesis of triphosphates from monophosphates in the paper by Donald E. Hoard and Donald G, Ott, J. Am. Chem. Soc. 1965, 87, 1785–1788.

The 5'monophosphate of 1-(2-deoxy-β-D-erythro-pentofuranosyl)-5-ethynyl uracil (0.61 mmol) was co-evaporated with 2×50 ml 0.5M triethylammonium bicarbonate at 40° C. on a rotary evaporator to a tan foam. The nucleotide was then co-evaporated with 3×75 ml of dry acetonitrile (Aldrich Chemical Co., Milwaukee, Wis.) in the same round-bottom flask. The nucleotide thus dried was dissolved in 5 ml of 1,3-dimethyl-3,4,5,6-tetrahydro-2(1H)-pyrimidinone (Aldrich) with magnetic stirring. Approximately 5 equivalents (498 mg) of 1,1'-carbonyldiimidazole was added to the solution and the mixture stirred for 1 h with the flask sealed with a serum stopper. At this time, 157 microliters of methanol was added and the solution stirred for 75 min to destroy excess 1,1'-carbonyldiimidazole.

1.2 Equivalents of 5'-chloro-2',5'-dideoxy-5-fluorouridine 3'-O-phosphate was co-evaporated with 0.5M triethylammonium bicarbonate, then dry acetonitrile as the previous nucleoside. The 5-fluoro nucleotide was then dissolved in 4 ml of 1,3-dimethyl-3,4,5,6-tetrahydro-2(1H)-pyrimidinone and added to the 5-ethynyl nucleotide phosphorimidazolidate mixture. This new mixture was allowed to stir overnight. The following day an additional 0.25 equivalent of the 5-fluoro nucleotide, similarly prepared, was added to the phosphorimidazolidate mixture and the resulting solution stirred over the weekend. This condensation mixture was then diluted into 150 ml aqueous ammonium hydroxide, pH 9.5; 500 microliters of alkaline phosphatase (Boehringer Mannheim, Indianapolis, Ind.) was added to cleave non-coupled nucleotides and the mixture was allowed to stir overnight. The following day, the alkaline solution was diluted to 600 ml total volume with water and loaded onto 80 g of DEAE Sephadex swollen in 50 mM ammonium bicarbonate. The column was eluted with an increasing gradient of aqueous ammonium bicarbonate (50 mM to 500 mM) with UV detection at 270 nm. Elution flowrate was controlled by Gilson Minipuls 2 peristaltic pumps (Gilson, Middleton, Wis.). Fractions were analysed by HPLC with a 4.6 mm×100 mm, 5 rnicron, analytical strong anion exchange column (Alltech, Deerfield, Ill.) and a linear gradient of 10 mM to 1M ammonium phosphate, pH 2.4, 5% methanol over 30 min. Pure product fractions were pooled and water was removed on a rotary evaporator. The resulting white solid was co-evaporated multiple times with water on the rotary evaporator, then re-dissolved in 15 ml of water, frozen and lyophilised to give 0.18 mmoles (30% yield) of the title product. Analytical HPLC (as above), $R_t$=5.62 min. Negative Ion FAB MS (dithioerythritol/dithiothreitol) (M-H)$^-$=657.0. $^{31}$P NMR (1 MHz, $^1$H decoupled, 85% phosphoric acid δ=0.0, D$_2$O) δ (−) 10.14 - (−) 10.27 (d, 1P, 5'-Phosphate, $J_{P,P}$=21.48 Hz), (−) 10.94 - (−) 11.08 (d, 1P, 3'-Phosphate, J=21.48 Hz) ($^{31}$P assignments made by $^1$H - $^{31}$P HMQC NMR pulse sequence). $^1$H NMR (400 MHz, D$_2$O) δ 8.05 (s, 1H, H6"), 7.80 (d, 1H, H-5, J=7.0 Hz) 6.17-6.15 (m - overlapping triplets, 2H, H1', and H1'''), 4.78-4.74 (m, 1H, H3'), 4.42-4.40(m - 5 lines, H3"), 4.32-4.28 (m, 1H, H4'), 4.08-4.04 (m, 1H, H4'''), 4.03-4.00 (m, 2H, H5'''a and H5'''b), 3.76-3.73 (m, 2H, H5'a and H5'b), 3.44 (s, 1H, acetylenic H), 2.50-2.20 (m overlapping, 4H, H2'a, H2'b, H2'''a and H2'''b).

The product was assayed for phosphorous according to procedure of B. N. Ames, *Methods Enzymol.* 1966, 8, 115–118.

EXAMPLE 4

Method (a) Animal Dosing and 5-FU Urinary Sampling

5-FU and 5-EU bases and nucleosides were dissolved in deionized HPLC grade water immediately prior to dosing. All animals were dosed once, p.o. via gastric gavage at the indicated mg/kg dose for each compound (See Results Section and Figures). 5-EU and 5-EU nucleosides were dosed to animals 0.5 hr prior to dosing with 5-FU and 5-FU nucleosides. Dosing was routinely performed between 11 am and 1 pm. An approximate volume of 300 μL was used for each dose. Rats were placed in individual Nalge metabolism cages, which separate urine and faeces, and continued on a 12 hr light/dark schedule post-dosing. Mice were treated post-dose in a similar manner with the exception that 5 mice were housed per cage.

Urine from each cage was collected into 0–24 hr and 24–48 hr post-dose fractions. Cages were rinsed with deionized water prior to collection of each fraction. The combined volume of urine and rinse was brought to a standard volume with deionized water.

(b) Quantitation of 5-FU by Reversed-Phase HPLC Analysis.

5 ml of a thoroughly mixed urine sample was filtered through a Millex GS 0.22 μm filter (Millipore, Bedford, Mass.) and frozen prior to HPLC analysis. 1 ml of the thawed primary filtered solution was diluted with 2 ml of water and particulates were removed from this diluted stock solution using a Centrifree micro partition system (Amicon Division, W. R. Grace and Co., Beverly Mass.). 100 μL of this solution was quantitated for 5-FU by HPLC on a Waters Associates System (Waters Associates, Milford, Mass.) equipped with a Waters 600E system controller, a Waters 600 solvent delivery system, a Waters model 712 WISP automated sample injector, a Waters 484 tuneable absorbance detector, and a Waters 991 photodiode array detector. For quantitiation of 5-FU in rat urine, HPLC was performed on a 250 mm×4.6 mm YMC AQ-303 S-5 120A ODS analytical column (YMC, Morris Plains, N.J.) or on a Microsorb C18 analytical column with identical dimensions (Rainin Instrument Co., Woburn, Mass.). For each analysis the columns were first eluted isocratic at 0.5 ml/min with aqueous 50 mM ammonium acetate buffer, pH 4.8, and 0.5% acetonitrile (Buffer A) for 25 min, followed by a linear gradient over 15 min to a 50% mixture with aqueous 50 mM ammonium acetate buffer, pH 4.8, and 60% acetonitrile (Buffer B). Over the next 5 min a linear gradient was run to 100% buffer B, followed by isocratic elution with buffer B for 20 min. A linear gradient was then eluted across the column over a 10 min period to 100% buffer A and held at a flow rate of 0.5 ml for 2 min. The column was then re-equilibrated in buffer A at a flow rate of 0.75 ml/min for 15 min and then returned to the original flow rate (0.5 ml/min) for 2 min prior to injection of the next sample. The effluent was monitored at 266 nm and 5-FU had a retention time of ca. 16.5 min. Data was collected on the Waters 991 diode array detector and a Digital Specialties microcomputer equipped with an in-house HPLC data analysis program (CHROM). The UV peak areas were integrated on these systems and compared to those of a standard curve prepared from known aqueous concentrations of 5-FU isocratically eluted across the Microsorb column with Buffer A. The molar extinction coefficient used for 5-FU was 7070 $M^{-1}cm^{-1}$ at a λmax of 266 nm.

Plots of UV peak area vs 5-FU concentration were linear between 5 μM and 100 μM. The total urinary recovery of 5-FU was determined by multiplication of the nmoles of 5-FU determined from the standard curve by the dilution factor of 3 (above) and by the standard volume of urine collected.

5-FU recovery in mouse urine was determined as above with three exceptions: a Phenomenex 5 μm Extrasil C-18 column (250mm×4.6 mm i.d.; Phenomenex, Torrance, Calif.) was used; an identical gradient with buffer A as aqueous 50 mM formic acid, pH 3.5, with 0.5% acetonitrile and buffer B as aqueous 50 mM formic acid, pH 3.5, with 60% acetonitrile was used; the standard curve was prepared by diluting known concentrations of 5-FU into undosed mouse urine and eluting with the latter described gradient and buffers, instead of isocratic conditions.

Results (a) Release and Quantification of 5-FU From Nucleosides.

Rats were predosed with 5-EU (2 mg/kg, p.o.) 0.5 hr prior to dosing with the 5-FU nucleosides as shown in Table 1. The 5-FU nucleosides were dosed at either 10 or 25 mg/kg. The arabinoside and 2',3'-dideoxyriboside required the higher dosing in order to detect and quantify urinary recovery of 5-FU. For all nucleoside examples, 5-FU was only detected in the 0–24 hr urine and not in the 24–48 hr urine sampling. The riboside and 2'-deoxyriboside are optimum in vivo releasers of 5-FU with a urinary recovery of 5-FU>65%.

TABLE 1

Urinary Recovery of 5-FU In Rats For Various 5-FU Containing Nucleosides

|  | Dose (mg/kg) | Predose | % 5-FU Recovery 0–24 hr Urine (Average of Two Experiments) |
| --- | --- | --- | --- |
| 5-FU | 5 | — | <5 |
| 5-FU | 5 | 2 | 52 |
| 5-FU | 25 | 0.03 | 43–63 |
| 5-FU Nucleosides |  |  |  |
| Riboside | 10 | 2 | 78 |
| 2'-deoxyriboside | 10 | 2 | 67 |
| Tegafur | 10 | 2 | 38 |
| 5'-chloro-2',5'-dideoxyriboside | 50 | 0.03 | 21 |
| Arabinoside | 25 | 2 | 6 |
| 2',3'-dideoxy riboside |  | 2 | <5 |

(b) Protection of 5-FU From DPD Catabolism by Release of 5-EU From Nucleosides.

As seen in FIG. 1, rats were orally predosed with 0.03 mg/kg 5-EU and with 0.03, 0.3 and 3.0 mg/kg of various 5-EU nucleosides, prior to dosing with 25 mg/kg 5-FU. 5-FU was observed and quantitated in only the 0–24 hr urine samples. Approximately 65% of the 5-FU dose was recovered unchanged in the urine for the 5-EU treated rats. Predosing rats with either the riboside or the 2'-deoxyriboside of 5-EU (≧0.03 mg/kg) allowed for high urinary recovery (>40%) of 5-FU. A direct dose response for urinary recovery of 5-FU was observed when the arabinoside or the 2'-deoxy-5'-monophosphate of 5-EU was used to deliver the DPD inactivator. Urinary recovery of 5-FU was <5% at all predoses of 2',3'-dideoxy-5-ethynyluridine.

(c) Urinary Recovery of 5-FU in Rats Dosed with the Succinate Linked Nucleoside

Rats were dosed 25 mg/kg 5-FU equivalent with the succinate linked nucleosides. Greater than 35% of the 5-FU in the original dose was recovered unchanged in the 0–24 hr urine. 5-FU was not detected in the 24–48 hr urine.

(d) Urinary Recovery of 5-FU in Mice Dosed with the Succinate linked Nucleosides.

For these studies mice were dosed with either 5 mg/kg 5-FU or given an equivalent dose of 5-FU via the succinate linked nucleoside. The urinary recovery of 5-FU was measured in the presence and absence of 5-EU (Table 2). Without predosing mice with 5-EU before delivering the base 5-FU, 5-FU could not be detected in the urine. When mice were predosed with 5-EU followed by dosing with 5-FU, the urinary recovery of 5-FU was 50%. Mice dosed with the succinate linked nucleoside gave 25–30% urinary recovery of 5-FU available from the linked compound. There was no improvement of 5-FU urinary recovery from mice that were predosed with 5-EU followed by dosing with the succinate linked nucleoside.

TABLE 2

| Dose 5 mg/kg equivalent 5-FU | Predose | Recovery 5-FU (%) |
|---|---|---|
| 5-FU | — | 0 |
| 5-FU | 2 mg/kg | 51 |
| 5-Ethynyl-5"-fluoro-3,3'"-O-succinylbis(1-(2-deoxy-β-D-erythropentofuranosyl)uracil | — | 28 |
| 5-Ethynyl-5"-fluoro-3,3'"-O-succinylbis(1-(2-deoxy-β-D-erythropentofuranosyl)uracil | 2 mg/kg | 23 |

EXAMPLE 5

Antitumour Studies

Method

In vivo antitumor testing with murine Colon 38 was conducted in-house. C57BL/6 female mice were housed in sterile, polycarbonate, filter-capped Microisolator cages (Lab Products, Inc., Maywood, N.J.) containing sterile hardwood bedding. Mice were fed sterile rodent chow and filter-sterilised water ad libitum. All manipulations of these mice were conducted in laminar-flow biosafety hoods. Colon 38 carcinoma was obtained from the Development Therapeutics Program Tumour Repository. Mice were implanted s.c. with 70 mg tumour fragments using a number 13 trocar. There were 10 mice in the control group that received tumour implants without drug treatment. There were 5 mice in each group treated with the dose and compounds as described below. Treatment began on day 16 post tumour implant and compounds were dosed once/day for 9 days. 5-FU was dosed at 15, 20, 25, 30, and 40 mg/kg.. The succinate linked nucleoside was dosed at 4.5, 8.9, 17.9, 26.8, 35.7 and 44.6 mg/kg. The molecular weight of the succinate linked nucleoside is 580.40 and the corresponding equivalents of 5-FU that were dosed with this compound were 1.0, 2.0, 4.0, 6.0, 9.0 and 10.0 mg/kg. A sample of 5-FU and the succinate linked nucleoside doses are indicated in Table 3. Tumour weights were calculated three times per week from measurements of tumour length and width. Antitumor activity was expressed as the days delay in tumour growth (T-C). T-C was calculated as the difference in the median of days for treated animals minus control animals for tumour mass to double twice post initial day of dosing (Day 16). Tumour-free survivors were not excluded from T-C calculations. Surviving mice were sacrificed after day 56.

Results

Antitumor Efficacy of 5-ethynyl-5"-fluoro-3.3'"-O-succinylbis(1-(2-deoxy-β-D-erythropentofuranosyl)uracil The effect of the succinate linked nucleoside was studied in mice with s.c. implants of Colon 38 vs therapy with 5-FU alone. Antitumor activity was expressed as tumour growth delay (T-C; see Methods). The succinate linked nucleoside was toxic at doses >17.9 mg/kg (4 mg/kg (4 mg/kg 5-FU and 5-EU equivalents). Table 3 shows a sub-optimum, effective and toxic dose for 5-FU and the succinate linked nucleoside.

TABLE 3

| Compound | Dose (mg/kg 5-FU equivalent) | Antitumour Activity T-C (Days) | Tumour-free Survivors (Day 56) |
|---|---|---|---|
| 5-FU | 25 | 14.9 | 0/5 |
| 5-FU | 30 | 23.6 | 0/5 |
| 5-FU | 40 | Toxic | 0/5 |
| * | 1 | 12.9 | 0/5 |
| * | 2 | >27.9 | 2/5 |

*=5-Ethynyl-5"-fluoro-3,3'"-O-succinylbis(1-(2-deoxy-β-D-erythropentofuranosyl)uracil)

We claim:

1. A compound selected from:
   5-ethynyl-5"-fluoro-3',3'"-O-succinylbis-(1-(2-deoxy-β-D-erythropento furanosyl)uracil);
   5-ethynyluridine-5-fluoro-1-(β-D-arabinofuranosyl) uracil succinic acid 5',2'-diester;
   5-fluoro-5"-(1-propynyl)-2',2'"-O-succinylbis(1-β-D-arabinofuranosyl)uracil); and
   5-chloro-2'-5'-dideoxy-5-fluorouridine-2'"-deoxy-5"-ethynyluridine (3'-5'")diphosphate.

2. A pharmaceutical composition comprising a compound selected from:
   5-ethynyl-5"-fluoro-3',3'"-O-succinylbis-(1-(2-deoxy-β-D-erythropento furanosyl)uracil);
   5-ethynyluridine-5-fluoro-1-(β-D-arabinofuranosyl) uracil succinic acid 5',2'-diester;
   5-fluoro-5"-(1-propynyl)-2',2'"-O-succinylbis(1-β-D-arabinofuranosyl)uracil); and
   5-chloro-2'-5'-dideoxy5-fluorouridine 2'"-deoxy-5'"-ethynyluridine (3'-5'")diphosphate
together with one or more pharmaceutically acceptable carriers.

3. A pharmaceutical composition according to claim 2 for oral administration.

* * * * *